United States Patent
Lehto (10) Patent No.: US 7,622,079 B2
(45) Date of Patent: Nov. 24, 2009

(54) DUAL NEST MICROPLATE SPOTTER

(75) Inventor: Dennis A. Lehto, Santa Clara, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 774 days.

(21) Appl. No.: 11/086,072

(22) Filed: Mar. 22, 2005

(65) Prior Publication Data

US 2006/0216207 A1    Sep. 28, 2006

(51) Int. Cl.
G01N 35/02 (2006.01)
G01N 35/04 (2006.01)
G01N 35/10 (2006.01)

(52) U.S. Cl. ............... 422/65; 422/63; 422/68.1; 422/100; 436/43; 436/47; 436/48; 436/49; 436/180

(58) Field of Classification Search ............ None
See application file for complete search history.

(56) References Cited

U.S. PATENT DOCUMENTS

| | | |
|---|---|---|
| 4,901,221 A | 2/1990 | Kodosky et al. |
| 4,914,568 A | 4/1990 | Kodosky et al. |
| 4,952,518 A | 8/1990 | Johnson et al. |
| 5,291,587 A | 3/1994 | Kodosky et al. |
| 5,301,301 A | 4/1994 | Kodosky et al. |
| 5,301,336 A | 4/1994 | Kodosky et al. |
| 5,481,741 A | 1/1996 | McKaskle et al. |
| 5,736,333 A | 4/1998 | Livak et al. |
| 5,985,214 A | 11/1999 | Stylli et al. |
| 6,001,309 A | 12/1999 | Gamble et al. |
| 6,082,797 A | 7/2000 | Antonette |
| 6,099,230 A | 8/2000 | Hitch |
| 6,220,451 B1 | 4/2001 | Hoffmann |
| 6,228,659 B1 | 5/2001 | Kowallis et al. |
| 6,299,840 B1* | 10/2001 | Watanabe et al. ............ 422/63 |
| 6,323,035 B1 | 11/2001 | Kedar et al. |
| 6,325,114 B1 | 12/2001 | Bevirt et al. |
| 6,371,717 B1* | 4/2002 | Grams et al. ........... 414/416.09 |
| 6,372,185 B1 | 4/2002 | Shumate et al. |
| 6,416,719 B1 | 7/2002 | Fawcett et al. |
| 6,420,180 B1 | 7/2002 | Bass |
| 6,447,723 B1 | 9/2002 | Schermer et al. |
| 6,468,800 B1 | 10/2002 | Stylli et al. |
| 6,472,218 B1 | 10/2002 | Stylli et al. |
| 6,479,301 B1 | 11/2002 | Balch et al. |
| 6,495,369 B1* | 12/2002 | Kercso et al. ................. 436/47 |
| 6,506,611 B2 | 1/2003 | Bienert et al. |
| 6,558,623 B1 | 5/2003 | Ganz et al. |
| 6,599,693 B1 | 7/2003 | Webb |
| 6,660,233 B1 | 12/2003 | Coassin et al. |

(Continued)

Primary Examiner—P. Kathryn Wright
(74) Attorney, Agent, or Firm—Leonard Bowersox (57) ABSTRACT

A fluid distribution system comprises a table configured to engage at least two microplates and moveable in an X-Y plane and in a Z direction toward and away from the X-Y plane. The fluid distribution system can comprise a dispensing head that comprises a plurality of dispensing tips adapted to dispense fluid to one or more locations of a microplate. A plate-handling device is provided to selectively pick up and deposit, substantially simultaneously, two or more of the microplates. The fluid distribution system can further comprise an accessory carriage configured to engage a source of fluid and move the source of fluid into a position adjacent the dispensing head in position for the dispensing head to aspirate fluid from the source of the fluid.

6 Claims, 10 Drawing Sheets

U.S. PATENT DOCUMENTS

| | | | |
|---|---|---|---|
| 6,669,432 B2 * | 12/2003 | Hamel et al. | 414/331.05 |
| 6,672,344 B1 | 1/2004 | Stokes et al. | |
| 6,678,577 B1 | 1/2004 | Stylli et al. | |
| 6,685,884 B2 | 2/2004 | Stylli et al. | |
| 6,752,182 B2 | 6/2004 | Atkinson et al. | |
| 2001/0046437 A1 * | 11/2001 | Bramwell et al. | 414/796.7 |
| 2002/0012611 A1 | 1/2002 | Stylli et al. | |
| 2002/0102149 A1 * | 8/2002 | Warhurst et al. | 414/267 |
| 2002/0119077 A1 | 8/2002 | Shumate et al. | |
| 2002/0173048 A1 | 11/2002 | Nakazawa et al. | |
| 2002/0176803 A1 | 11/2002 | Hamel et al. | |
| 2002/0182117 A1 | 12/2002 | Coassin et al. | |
| 2003/0017085 A1 | 1/2003 | Kercso et al. | |
| 2003/0032198 A1 | 2/2003 | Lugmair et al. | |
| 2003/0124735 A1 | 7/2003 | Nanthakumar et al. | |
| 2003/0161761 A1 | 8/2003 | Williams et al. | |
| 2004/0062686 A1 * | 4/2004 | Ganz et al. | 422/100 |

* cited by examiner

DUAL NEST MICROPLATE SPOTTER

INTRODUCTION

The present application generally relates to automated systems and methods for dispensing fluids, for example, to a plurality of microplates. There is a need for a fluid distribution system that can rapidly and accurately dispense fluids to a plurality of microplates.

SUMMARY

According to various embodiments, a fluid distribution system is provided for distributing fluids to a plurality of microplates. The fluid distribution system can comprise a table configured to engage at least two microplates and that can be moveable in an X-Y plane and in a Z direction toward and away from the X-Y plane. The fluid distribution system can comprise a dispensing head adapted to dispense fluids to a microplate, and to aspirate fluids from a source of fluid. A plate-handling device can be provided to selectively pick up and deposit two or more microplates, for example, to substantially simultaneously pick-up one microplate and drop-off another microplate. The fluid distribution system can further comprise an accessory carriage configured to engage a source of fluid and move the source of fluid into a position adjacent the dispensing head to enable aspiration of fluid from the source of fluid into a plurality of dispensing tips of the dispensing head.

According to various embodiments, a fluid distribution system is provided that can comprise a pair of microplate holders mounted on a three-axis slide carriage, wherein the slide carriage can be mounted for movement on a track. The three-axis slide carriage can be adapted to move the microplate holders in any one or more of three orthogonal directions, for example, in any one or more of an X, a Y, and a Z direction. A fluid dispensing or spotting head can be provided in a fixed position relative to the track and can comprise a plurality of dispensing tips that can each comprise a fluid dispenser, a fluid aspirator, or both a fluid dispenser and a fluid aspirator. A plate-handling device can also be provided, for example, comprising at least two sets of jaws including at least one set positioned above at least one other set.

According to various embodiments, a method of distributing fluids to a plurality of microplates can comprise moving at least two microplates on a table into relationship with a fluid dispensing head comprising a plurality of dispenser tips, such that at least a first of the at least two microplates can be positioned to receive fluid from the dispensing head while at least a second of the at least two microplates can be accessible by a plate-handling device. The method can further comprise dispensing fluid from the dispensing head to a plurality of locations on the first microplate while the second of the microplates can be exchanged with a new plate using the plate-handling device. According to various embodiments, the method can further comprise moving the pair of microplates away from the head, moving a source of fluid into a position adjacent the dispensing head, and aspirating fluid from the source of fluid into the plurality of dispensing tips of the dispensing head.

Additional features and advantages of the present teachings will be set forth in part in the description that follows, and in part will be apparent from the description, or can be learned by practice of the present teachings.

DRAWINGS

The skilled artisan will understand that the drawings, described below, are for illustration purposes only. The drawings are not intended to limit the scope of the present teachings in any way.

It is to be understood that both the foregoing general description and the following detailed description are exemplary and explanatory only and are intended to provide a further explanation of the present teachings.

DESCRIPTION OF VARIOUS EMBODIMENTS

The headings (such as "Introduction" and "Summary,") and sub-headings used herein are intended only for general organization of topics within the disclosure of the present teachings, and are not intended to limit the disclosure of the present teachings or any aspect thereof. In particular, subject matter disclosed in the "Introduction" can include aspects of technology within the scope of the present teachings, and can not constitute a recitation of prior art. Subject matter disclosed in the "Summary" is not an exhaustive or complete disclosure of the entire scope of the teachings or any embodiments thereof.

The citation of references herein does not constitute an admission that those references are prior art or have any relevance to the patentability of the teachings disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the teachings, are intended for purposes of illustration only and are not intended to limit the scope of the teachings. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of these teachings and, unless explicitly stated otherwise, are not intended to be a representation that given embodiments of these teachings have, or have not, been made or tested.

As used herein, the word "include," and its variants, is intended to be non-limiting, such that recitation of items in a list is not to the exclusion of other like items that can also be useful in the materials, compositions, devices, and methods of the present teachings.

In order to facilitate use with existing equipment, robotic implements, and instrumentation, the dimensions or footprint of main body 40 and/or skirt portion 42 of microplate 22 should conform to standards specified by the Society of Biomolecular Screening (SBS) and the American National Standards Institute (ANSI) published January 2004 (ANSI/SBS 3-2004), incorporated by reference herein. Microplate 22 can include additional alignment features 31, which can include slots, pins, cut corners, indentations, graphics, protrusions (nubs) or combinations thereof. These alignment features can be placed so that they do not interfere with a sealing cover or wells; however, by locating such alignment features near wells, improved alignment with dispensing equipment and/or a thermocycler block can be achieved.

The microplate can include an alignment feature as a corner chamfer; however, it should be understood that the alignment feature can be a pin, slot, or other unique feature that can be capable of interfacing with a corresponding feature formed in a fixture, reagent dispensing equipment, and/or thermocycler. In other embodiments, the alignment feature can be a nub or protrusion. In such embodiments, the length dimension of the microplate can be about 127 mm measured from the tangent point of one nub to the tangent of the opposite nub and the width of about 85 mm can be calculated in the same fashion.

The microplate can be made from any one of a number of materials, for example, by non-limiting example, glass, ceramic, silicon, standard plastic, plastic compounded with a thermally conductive material, polypropylene, polystyrene, polyethylene, polyethyleneterephthalate, styrene, acrylonitrile, cyclic polyolefin, syndiotactic polystyrene, polycarbonate and liquid crystal polymer or any plastic material known to those skilled in the relative art with a melting point greater than 130° C. and exhibiting a very low fluorescence when exposed to visible or non-visible light. Conductive material, for example, a conductive carbon black or other conductive filler known to those skilled in the relative art, can be included in the formulation of the plastic to increase thermal conductivity. "Thermal conductivity" can be defined as the heat flow across a surface per unit area per unit time, divided by the negative of the rate of change of temperature with distance in a direction perpendicular to the surface. Thermal conductivity can be also known as heat conductivity. Alternatively, thermal conductivity can generally be thought of as the rate at which heat can be conducted through a substance. The thermal conductivity of the microplate improves heat distribution, thereby improving the heating and cooling of an assay therein. To further increase the thermal conductivity, thermally conductive ceramic filler, for example, boron nitrate filler or other ceramic filler, can be added to the formulation. It should be understood that combinations of these different materials can be used. In various embodiments, the microplate can be co-molded such that the bottom of the wells comprise a metal, a clear material, a glass, a quartz, tin iridium oxide, a different plastic composition or the like.

The microplate can be made of an electrically conductive material, which can improve reagent dispensing alignment. In this regard, electrically conductive material can serve to minimize static build-up on the microplate so that the reagent droplets do not go astray during dispensing. In some embodiments, a voltage can be applied to pull the sample into the appropriate position, particularly with a co-molded part where the flat "bottom" section can be electrically conductive and the sides of the wells can be not electrically conductive. In other embodiments, a high voltage field can be applied under the well or well of interest to pull the sample into the appropriate wells.

In order to increase throughput of genotyping, gene expression, and other assays, the microplate can include a dramatically increased density of wells beyond that employed in the prior art. For example, the microplate has been proven using 6,144 wells, while prior art designs have been limited to no more than 1,536 wells. It should be appreciated, however, that assays used in the microplate are not limited to DNA assays that can be homogenous, for example, TAQMAN® and INVADER®, but could also include other assays, for example, receptor binding, enzyme, and other high throughput screening assays. The microplate 22 can also be used for the temporary storage of reagents, samples, and other related applications.

The present teachings relate to processing microplates with any well array configuration essentially within the standard SBS footprint. In various embodiments, the microplates can be, but are not limited to, any of the well array parameters described in Table 1.

TABLE 1

| Total Wells | Rows × Columns | Approximate Well Area |
|---|---|---|
| 96 | 8 × 12 | 9 × 9 mm |
| 384 | 16 × 24 | 4.5 × 4.5 mm |
| 1536 | 32 × 48 | 2.25 × 2.25 mm |
| 3456 | 48 × 72 | 1.5 × 1.5 mm |
| 6144 | 64 × 96 | 1.125 × 1.125 mm |
| 13824 | 96 × 144 | 0.75 × .075 mm |
| 24576 | 128 × 192 | 0.5625 × 0.5625 mm |
| 55296 | 192 × 288 | 0.375 × 0.375 mm |
| 768 | 24 × 32 | 3 × 3 mm |
| 1024 | 32 × 32 | 2.25 × 3 mm |
| 1600 | 40 × 40 | 1.8 × 2.7 mm |
| 1280 | 32 × 40 | 2.25 × 2.7 mm |
| 1792 | 32 × 56 | 2.25 × 1.714 mm |
| 2240 | 40 × 56 | 1.8 × 1.714 mm |
| 864 | 24 × 36 | 3 × 3 mm |

TABLE 1-continued

| Total Wells | Rows × Columns | Approximate Well Area |
|---|---|---|
| 4704 | 56 × 84 | 1.257 × 1.257 mm |
| 7776 | 72 × 108 | 1 × 1 mm |
| 9600 | 80 × 120 | 0.9 × .09 mm |
| 11616 | 88 × 132 | 0.818 × 0.818 mm |
| 16224 | 104 × 156 | 0.692 × 0.692 mm |
| 18816 | 112 × 168 | 0.643 × 0.643 mm |
| 21600 | 120 × 180 | 0.6 × 0.6 mm |
| 27744 | 136 × 204 | 0.529 × 0.529 mm |
| 31104 | 144 × 216 | 0.5 × 0.5 mm |
| 34656 | 152 × 228 | 0.474 × 0.474 mm |
| 38400 | 160 × 240 | 0.45 × 0.45 mm |
| 42336 | 168 × 252 | 0.429 × 0.429 mm |
| 46464 | 176 × 264 | 0.409 × 0.409 mm |
| 50784 | 184 × 256 | 0.391 × 0.391 mm |

During analysis, each well can include an assay. As described above, the assay can comprise a reaction solution, which can be a homogenous solution and can comprise a sample, two primers, at least one labeled probe, internal standard Taq polymerase, and a buffer in the solution. For example, see U.S. Pat. No. 5,736,333 issued April 1998. The assay components can comprise sufficient components to perform a homogenous assay after adding only a sample. According to some embodiments, the components for carrying out a homogeneous assay can comprise components sufficient to achieve a coupled amplification and detection wherein the process of amplification generates a detectable signal and subsequent sample handling and manipulation to detect the amplified product can be minimized or eliminated. According to some embodiments, the components can enable a method wherein amplification is detectable without opening the reaction chamber, and without further processing steps once amplification is initiated.

The plurality of wells of the microplate can have any cross-sectional shape. For example, the plurality of wells can define a generally circular rim portion with downwardly-extending, generally continuous sidewall that terminates at a bottom wall in a radius. To ease manufacturing, a draft angle of the sidewall can be used. The particular draft angle can be determined by the manufacturing method and the size of the well. By way of a non-limiting example, circular rim portion can be about 1.0 mm in diameter, the depth of the well can be about 0.9 mm, the draft angle of the sidewalls can be about 1° to more than 5° and each well can be spaced about 1.125 mm from center to center. In certain embodiments, the volume of each well can be about 500 nL.

Alternatively, the plurality of wells can define a generally square-shaped rim portion with downwardly extending sidewalls that terminate at a bottom wall. To ease manufacturing and to minimize shadowing, a draft angle of the sidewalls can be used. Again, the particular draft angle can be determined by the manufacturing method and the size of the well. By way of non-limiting example, side dimensions of a portion can be about 1.0 mm in length, the depth of well can be about 0.9 mm, the draft angle of the sidewalls can be about 1° to more than 5°, and each well 34 can be spaced about 1.125 mm from center to center. In certain embodiments, the volume of each well can be about 500 nL. In various embodiments, the spacing between wells as measured at the top of a wall dividing wells can be less than about 0.5 mm. In certain embodiments, this spacing between wells can be about 0.25 mm.

The following description of the embodiments is merely exemplary in nature and is in no way intended to limit the teachings, their application, or uses. For example, the present teachings can find utility in a wide variety of applications, for example, in connection with Polymerase Chain Reaction (PCR) measurements; ELISA tests; DNA and RNA hybridizations; antibody titer determinations; protein, peptide, and immuno tests; recombinant DNA techniques; hormone and receptor binding tests; and the like. Additionally, the present teachings can be particularly well suited for use with luminescence, calorimetric, chemilumescence, or radioactivity measurement, for example, scintillation measurements. Although the present teachings are discussed in further detail below in relation to Polymerase Chain Reaction measurements, such enabling discussion should not be regarded as limiting the present teachings to only such applications.

Other microplates, systems for processing them, and components for such systems, can be found, for example, in U.S. Provisional Application No. 60/504,052 filed on Sep. 19, 2003; U.S. Provisional Application No. 60/504,500 filed on Sep. 19, 2003; U.S. Provisional Application No. 60/589,224 filed Jul. 19, 2004; U.S. Provisional Application No. 60/589,225 filed on Jul. 19, 2004; U.S. patent application Ser. No. 10/913,601 filed on Aug. 5, 2004 and U.S. Provisional Application No. 60/601,716 filed on Aug. 13, 2004, all of which are incorporated herein in their entireties by reference. A1

Figure 1:
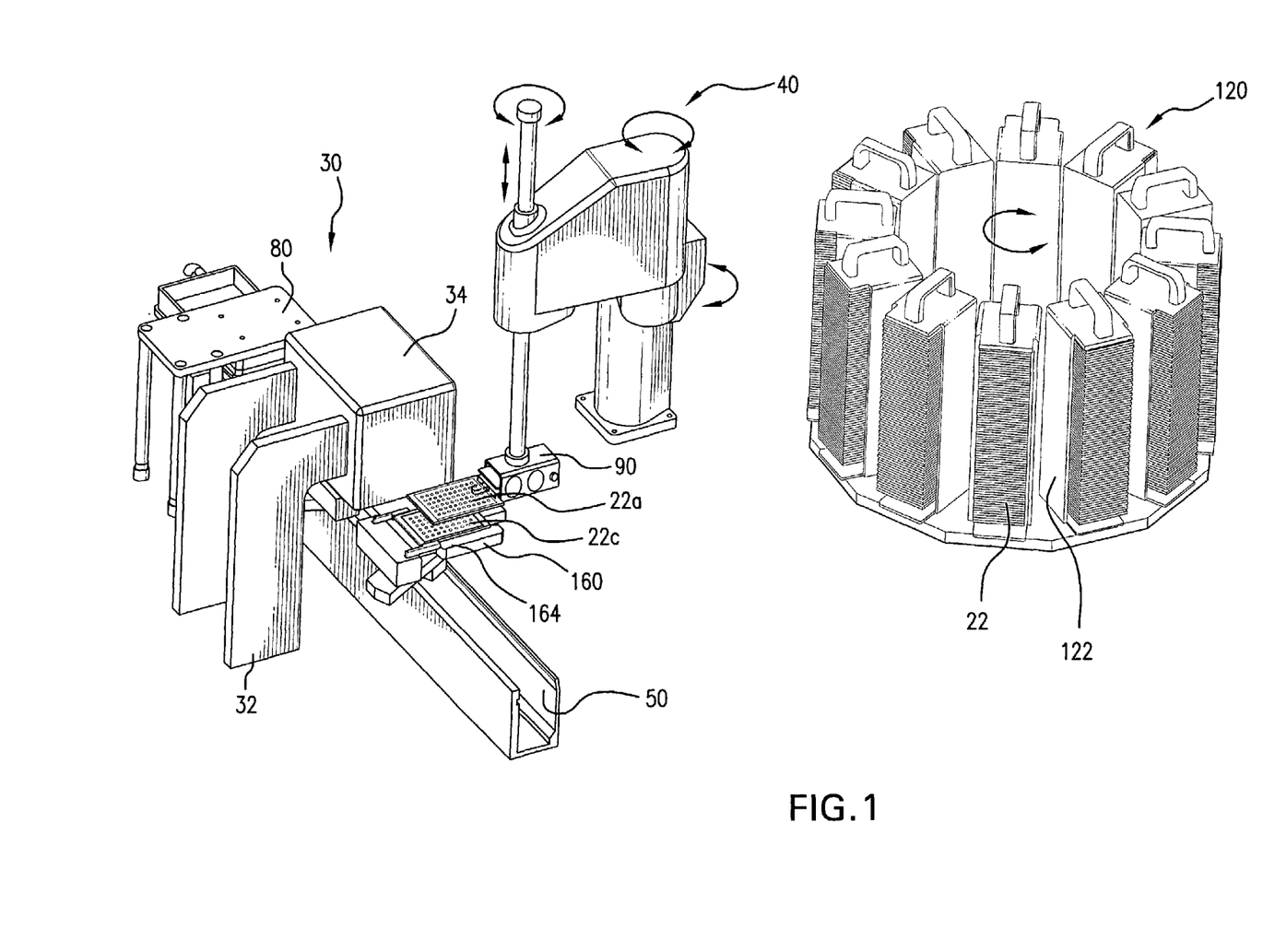
FIG. 1 illustrates a perspective view of an embodiment of a fluid distribution system comprising a carousel comprising racks or hotels of microplates, a robotic plate-handling mechanism, and a fluid dispensing head for dispensing fluid to locations of a selected microplate.

Referring to FIG. 1, various embodiments of a system and method can be described for handling microplates for biological assay plate spotting. According to various embodiments, a system and method can be provided to increase the number of microplates that can be processed in a period of time by decreasing the amount of time to shuttle the microplates into and out of position with respect to one or more dispensing and/or aspirating heads by enabling a dispensing operation that takes place at the same time as microplates are transferred to and from a plate-handling device. The plate-handling device (40) can load into and unload from a microplate storage facility (120) and the fluid dispensing and/or aspirating head (34). As shown in FIG. 1, and according to various embodiments, a plurality of microplates 22 can be stacked in hotels 122 that can be arranged round and make-up part of a carousel 120. A robotic assembly 40 can comprise a plate gripper robot 90 that can be progranmably controlled to move the microplates 22 between the hotels of carousel 120 and a loading and unloading position adjacent a fluid dispensing device 30. Robotic assembly 40 can comprise, for example, a Select Compliant Articulated Robot Arm (SCARA) robot available from IAI America, Inc. of Torrance, Calif. Fluid dispensing device 30 can comprise a spotter head 34 mounted with supports 32 in relation to a track 50. The relation can be a fixed relation or an adjustable relation with respect to the track 50. As is described in greater detail below, plate gripper robot 90 can exchange two microplates, 22a and 22b, from a nest 164 on or in a carriage or table 160. Also adjacent spotter head 34 can be positioned an accessory station 80 in fixed or adjustable relation with respect to track 50.

Figure 2:
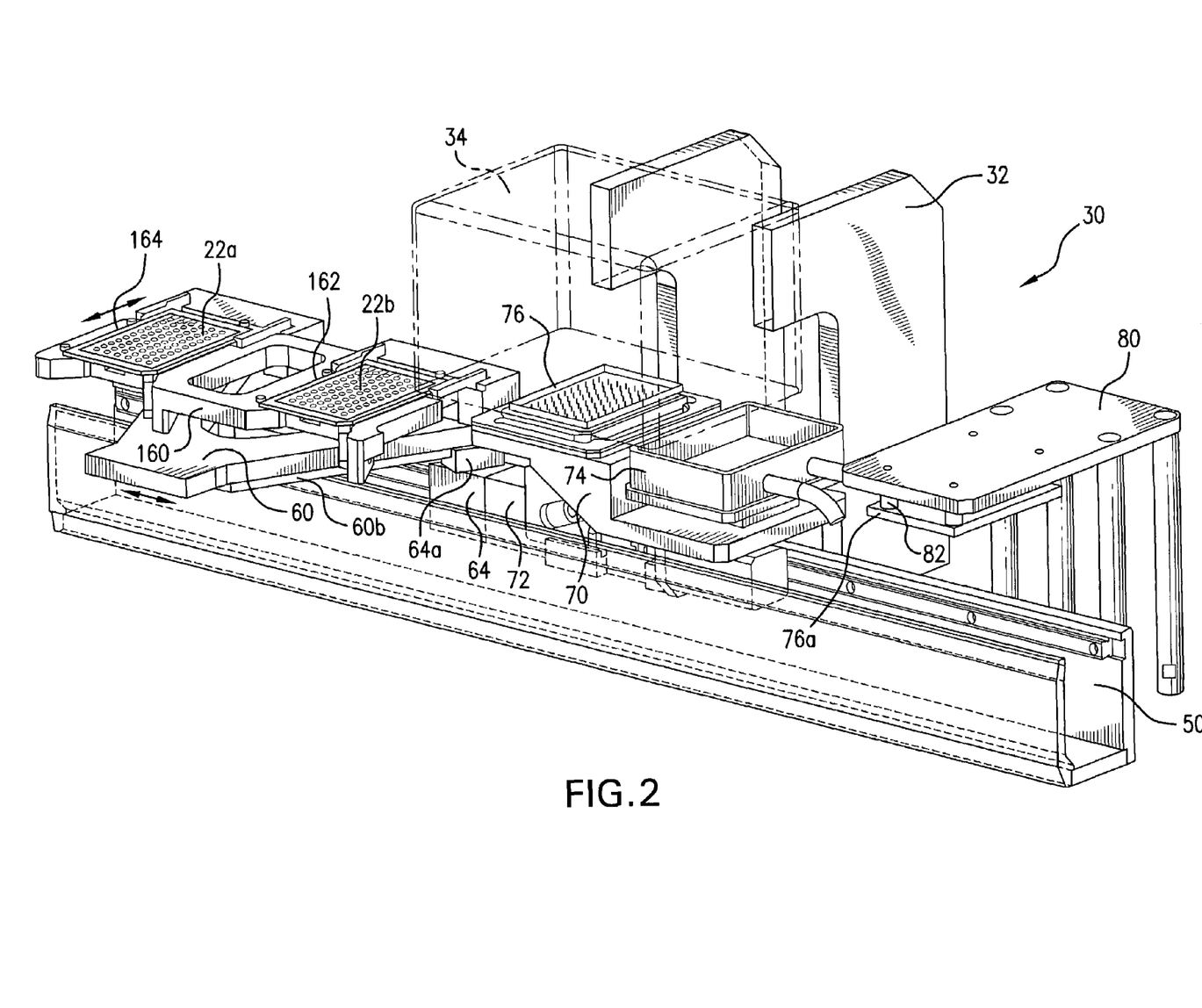
FIG. 2 illustrates a perspective view of an embodiment comprising a slide carriage holding two microplates and an accessory carriage holding a fluid source plate, with both carriages positioned for movement on a track and relative to a fixed fluid dispensing head that can be adapted to dispense and/or aspirate fluid.
Figure 3:
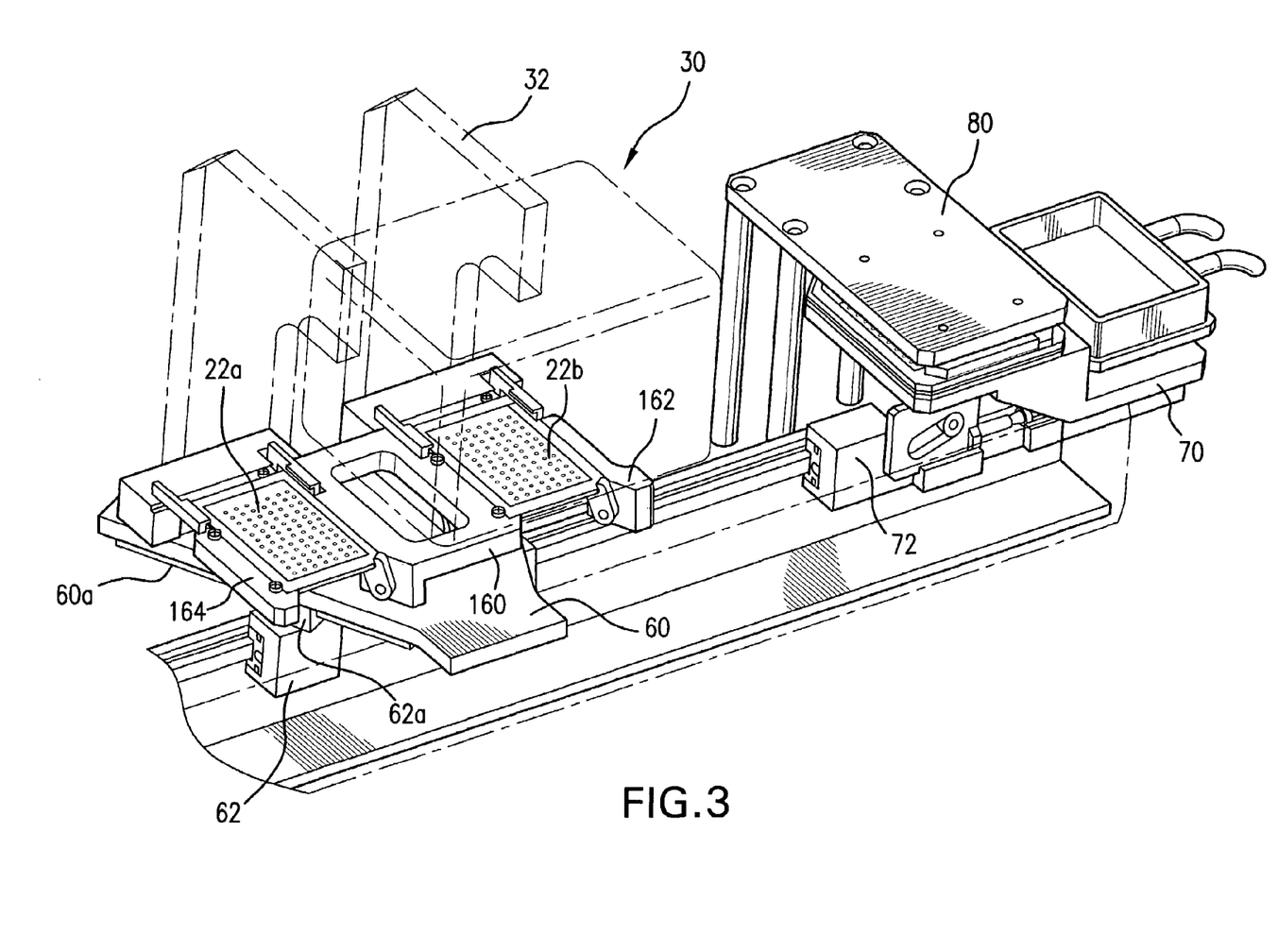
FIG. 3 illustrates a perspective view of the embodiment shown in FIG. 2, wherein the main slide carriage can be positioned under the fixed fluid dispensing head and the accessory carriage can be positioned away from the dispensing head.

Referring to FIG. 2 and FIG. 3, and according to various embodiments, fluid dispensing device 30 can include spotter head 34 that in-turn can comprise a plurality of fluid dispensing and/or aspirating tips or elements that can be adapted to dispense very precise and small or micro amounts of fluid, for example, less than 1 milliliter at a time. The tips can be tuned to dispense fluids to predetermined locations on a microplate, as well as to aspirate or suck-in fluid from a source of fluid in preparation for dispensing the fluid to a microplate. The amounts of fluid that can be precisely dispensed by each of the elements of spotter head 34 can be measured in nanoliters or pico liters.

A slide carriage 60 can be mounted on track 50, with slide carriage 60 providing support for a top plate 160 that can comprise a pair of microplate nests 162, 164. Slide carriage 60 can be provided with two horizontal axes of motion by linear motor driven carriages 62 and 64 mounted on track 50 and comprising rail engagement portions 62a and 64a that engage with angled rails 60a and 60b along the underside of slide carriage 60. Rails 60a and 60b can be formed integrally with slide carriage 60, or can be attached using any of a number of different known methods of attachment including, but not limited to, bolting, welding, brazing, soldering, or otherwise attaching, to the bottom of slide carriage 60. Rails 60a and 60b can be oriented at any of a number of different angles with respect to a center line of the top plate 160, for example, about 35 degrees, from about 25 degrees to about 45 degrees, from about 5 degrees to about 35 degrees, or from about 30 degrees to about 50 degrees. The rail engagement portions 62a and 64a of linear motor driven carriages 62 and 64 can comprise blocks comprising slots that receive the respective rails 60a and 60b, and anti-friction components (not shown) including, but not limited to, rollers or recirculating ball bearings, that engage with the rails 60a and 60b. With respect to the track, one of rails 60a and 60b can be oriented at an acute angle and one of rails 60a and 60b can be oriented at an obtuse angle. According to various embodiments, a base slide assembly comprising slide carriage 60 and track 50 is available from Belt-Everman, Inc. of Goleta, Calif.

As shown in FIGS. 2 and 3, the linear motor driven carriages 62 and 64 can be mounted for movement along track 50, while their respective rail engagement portions 62a and 64a remain engaged with angled rails 60a and 60b along the underside of slide carriage 60. Accordingly, if the two linear motor driven carriages 62 and 64 can be moved in unison and in the same direction along rail 50, slide carriage 60 including top plate 160 and the pair of microplate nests 162 and 164, moves along track 50. If linear motor driven carriages 62 and 64 are moved relative to each other, for example, by moving the two linear motor driven carriages 62 and 64 toward or away from each other, slide carriage 60 can move in a direction substantially perpendicular or perpendicular to track 50. Rail engagement portions 62a and 64a of respective linear motor driven carriages 62 and 64 move along angled rails 60a and 60b of slide carriage 60.

Top plate 160 of slide carriage 60 can also provide for a third vertical axis of motion, for example, through the use of short stroke air cylinders, linear motors, cams, or other actuators (not shown) to move top plate 160 in a vertical direction relative to slide carriage 60. Alternatively, the entirety of slide carriage 60 could be moved in a vertical direction relative to track 50, for example, by moving slide carriage 60 in a vertical direction relative to rail engagement portions 62a and 64a of slide carriage 60, using air cylinders or other actuation means. The vertical motion of top plate 160 of slide carriage 60 can be between two fixed positions. Top plate 160 can be moved up to allow for spotting or dispensing of fluid from spotter head 34 to locations on microplates nested on top plate 160. Top plate 160 can be moved down for shifting nests 162 and 164 toward and away from spotter head 34.

The two horizontal axes of motion provided by moving linear motor driven carriages 62 and 64 relative to each other can be programmed to any position within their range of motion. Programmable control of the movement of slide carriage 60 and microplates supported on top plate 160 of slide carriage 60 allows the spotting or dispensing of fluid to the microplates to be done in several stages. At each stage the position of a microplate supported on top plate 160 relative to spotter head 34 can be shifted slightly to bring a new set of location on the microplate into alignment with fluid dispensing elements (not shown) of spotter head 34. The number of locations on a microplate can be greater than the number of fluid dispensing elements of spotter head 34. For example, the wells on a microplate can be more closely or densely spaced than the fluid dispensing elements of spotter head 34. The fluid dispensing element can be disposed with a pitch that can be a multiple of a pitch of the number of wells. The multiple can be, for example, 2, 4, 8, 16, or more. Programmable movement of slide carriage 60 and microplates supported in dual nests 162 and 164 of top plate 160 of slide carriage 60 can result in each spotting cycle of spotter head 34 depositing spots in an interleaved subset of the wells on the microplate.

As shown in FIG. 3, top plate 160 of slide carriage 60 can comprise two nests 162 and 164 for locating and holding two microplates 22a and 22b. As shown in more detail in FIG. 6A, top plate 160 can comprise two nests 162 and 164, with nest 162 comprising three locating pins 162a, 162b, and 162c, and with nest 164 similarly comprising three locating pins 164a, 164b, and 164c. Microplates 22a and 22b can be positioned in nests 162 and 164 by the respective locating pins and can be gripped by nest-mounted plate grippers 163a and 163b. Plate grippers 163a and 163b can be adapted to grip microplate 22b in nest 162, and plate grippers 165a and 165b can be adapted to grip plate 22a in nest 164. A plate engagement ratchet, for example, ratchet 164d at nest 164 and ratchet 162d at nest 162, shown in FIG. 6A, can be provided to engage and locate the respective microplate 22a and 22b positioned in the respective nest 164, 162. The plate engagement ratchets 164d and 162d can rotate away from the respective microplate 22a and 22b when the plate grippers 165a and 165b, or 163a and 163b grip the respective microplate 22a and 22b and lift it from the respective nest 164, 162, as shown with regard to microplate 22a in FIG. 6B. Microplates 22a and 22b can comprise an alignment feature, for example, a chamfered corner 21a and 21b, respectively. Ratchet 164d coupled with locating pins 164a, 164b, and 164c and the chamfered corner 21a can accurately and securely position microplate 22a in nest 164. This disposition can assist in spotting microplate 22a. This disposition can assist in depositing and removing the microplate 22a from nest 164. The microplate can be similarly located or positioned in nest 162.

As shown in FIG. 1 and FIG. 3, nest 162 of top plate 160 on slide carriage 60 can be located under spotter head 34 for dispensing of fluid to locations of microplate 22b held in nest 162. At the same time, nest 164 can be accessible to a plate gripper robot 90 that can remove microplate 22a, while simultaneously or substantially simultaneously replacing microplate 22a with another microplate 22c.

Figures 4, 4B:
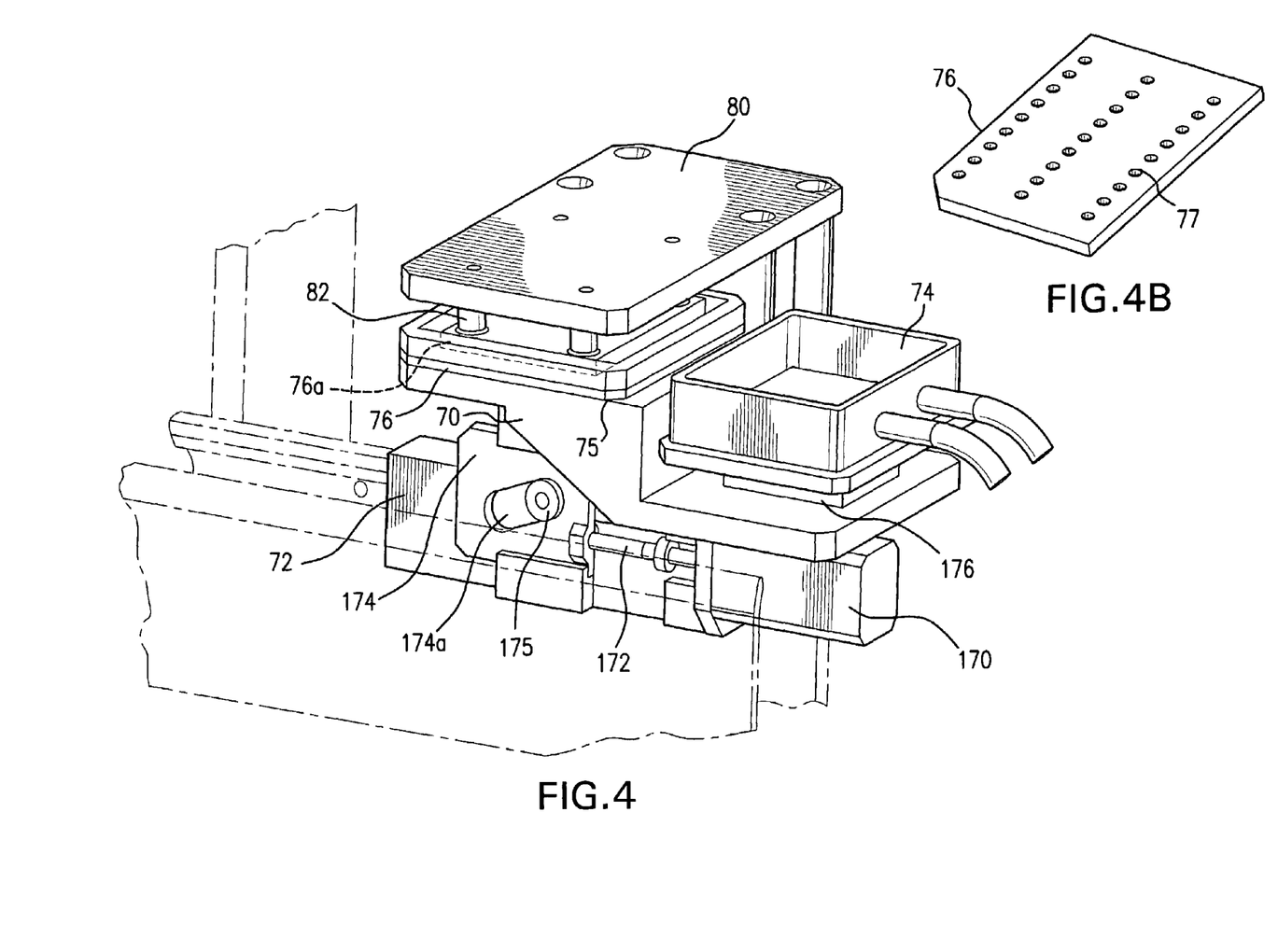
FIG. 4 illustrates a perspective view of the accessory carriage shown in FIGS. 2 and 3 and positioned to one side of the fixed fluid dispensing head, with the accessory carriage supporting a fluid source plate and a wash station.
FIG. 4B illustrates a perspective view of a source plate, according to various embodiments.

As shown in FIGS. 2 and 4, an accessory carriage 70 can also be mounted on the same track 50 as slide carriage 60. The accessory carriage 70 can hold a source plate 76 that can be used to replenish the spotter elements or fluid dispensing/aspirating elements of spotter head 34. Accessory carriage 70 can comprise a wash station 74 that can be used to clean the spotter elements or fluid dispensing/aspirating elements. Wash station 74 can be used in any manner desired to prevent cross-contamination of the microplates 22. For example, if desired, the fluid dispensing/aspirating elements in spotter head 34 can be cleaned after each fluid dispense, or before aspiration, or only if a source fluid or a source plate used to aspirate fluid dispensing/aspirating elements changes. The latter contemplates multiple dispensions of a fluid from a source; the multiple dispensions can be performed using one or more aspirations from the same source fluid. Different source plates 76 can be provided to accessory carriage 70. Each source plate 76 can comprise a different fluid to be loaded into the fluid dispensing/aspirating elements of spotter head 34. Each well on each source plate 76 can comprise a different fluid.

According to various embodiments, and as shown in FIG. 2, accessory carriage 70 can be moved along track 50 by engagement of a track mounted portion 72 of accessory carriage 70 with linear motor driven carriage 64 of slide carriage 60. In such an embodiment, slide carriage 60 can be used to tow accessory carriage 70 along track 50. Track-mounted portion 72 of accessory carriage 70 can be engaged with linear motor driven carriage 64 magnetically, or using other means of engagement for example, a releasable latching mechanism, or the like.

As shown in FIG. 4, accessory carriage 70, can also be provided with a motor 170, a lead screw 172, and a cam plate 174 that move platform 75 of accessory carriage 70 in a vertical direction to various programmable positions. Platform 75 of accessory carriage 70 can support source plate 76 against a source plate cover 76a that can be held in position at a fixed accessory station 80 by suction cups 82.

Accessory carriage 70 can be provided with a wash station 74 supported on an air powered slide 176 that can be adapted to shift the position of wash station 74 a short distance between two set positions. When accessory carriage 70 is moved to a position below spotter head 34, wash station 74 can provide a means for cleaning the fluid dispensing/aspirating elements of spotter head 34 by vertical movement of wash station 74 into position to allow aspiration of wash liquid into the fluid dispensing/aspirating elements and to allow ejection of wash liquid from the fluid dispensing/aspirating elements back into wash station 74 and into a drain. Wash station 74 can be shifted by air powered slide 176 between the two positions to position the fluid dispensing elements of spotter head 34 for such a cleaning process because spotter head 34 can be held in a fixed position by its supports 32.

While a source plate 76 positioned on platform 75 of accessory carriage 70 is waiting for the next aspirate step, accessory platform 75 of accessory carriage 70 can be elevated to a position where source plate 76 can be pressed against a source plate cover 76a held in position at the accessory station 80 by vacuum cups 82. Movement of accessory platform 75 in a vertical direction can be achieved by operation of a motor 170 to move a lead screw 172 attached to a cam plate 174 relative to track 50 and relative to track-mounted portion 72 of accessory carriage 70. This motion thereby causes a cam 175 mounted within a groove 174a of cam plate 174 to move vertically relative to the track 50, and thus move accessory platform 75 in a vertical direction. Movement of accessory platform 75 vertically upward while accessory carriage 70 is positioned at accessory station 80 presses source plate 76 against source plate cover 76a, and prevents evaporation of the fluid contained within the source plate 76. When the source plate is moved along with accessory carriage 70 from accessory station 80 to a position underneath spotter head 34, source plate lid 76a stays behind and can be held by vacuum cups 82 at accessory station 80. FIG. 4B illustrates the source plate 76 and a plurality of wells 77.

Figure 5:
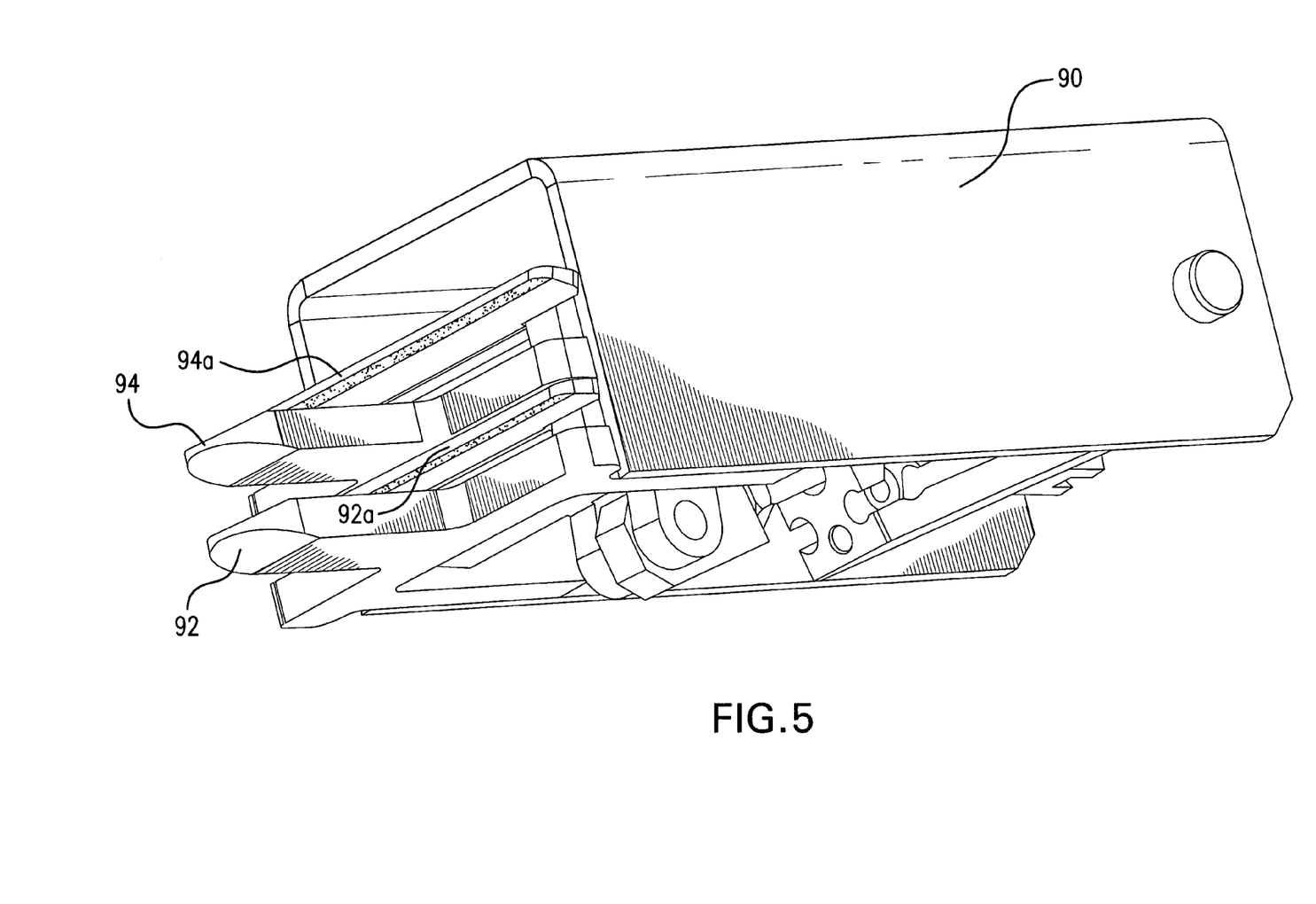
FIG. 5 illustrates a perspective view of a plate gripper robot according to various embodiments.

As shown in FIGS. 1, 5, 7, and 9, a plate gripper robot 90 can be manipulated by robotic assembly 40 into position relative to carousel 120 and relative to slide carriage 60. While in carousel 120, many microplates 22 can be supported in slots in each respective hotel 120. While in slide carriage 60, the microplates 22 can be supported on top plate 160 of slide carriage 60. Plate gripper robot 90 can be used to move microplates 22 toward and away from nests 162 and 164 of top plate 160 on slide carriage 60, and toward and away from hotels 122 of carousel 120. As shown in FIG. 5, plate gripper robot 90 has two sets of jaws, a lower jaw set 92, 92a and an upper jaw set 94, 94a. Upper jaw set 94, 94a can be mounted above lower jaw set 92, 92a. Lower jaw set 92, 92a comprises a lower jaw 92 adapted to slide underneath a first microplate 22 while the microplate resides in hotel 120, allowing a lower jaw plate clamping portion 92a to clamp down and grab the first microplate. Similarly, upper jaw set 94, 94a comprises a lower jaw 94 adapted to slide underneath a second microplate 22 allowing an upper jaw plate clamping portion 94a to clamp down and hold second microplate 22. This arrangement can allow plate gripper robot 90 to pick up first microplate 22 and deposit second microplate 22 in hotel 120 or in one of nests 162 and 164. The clamping of the first microplate can occur simultaneously or substantially simultaneously with an unclamping of the second microplate. The substantially simultaneous drop-off and pick-up can reduce two robot motion cycles to one cycle for the robotic assembly 40. The substantially simultaneous drop-off and pick-up can eliminate or mitigate a shift of plate gripper robot 90 to another position.

Figure 6A:
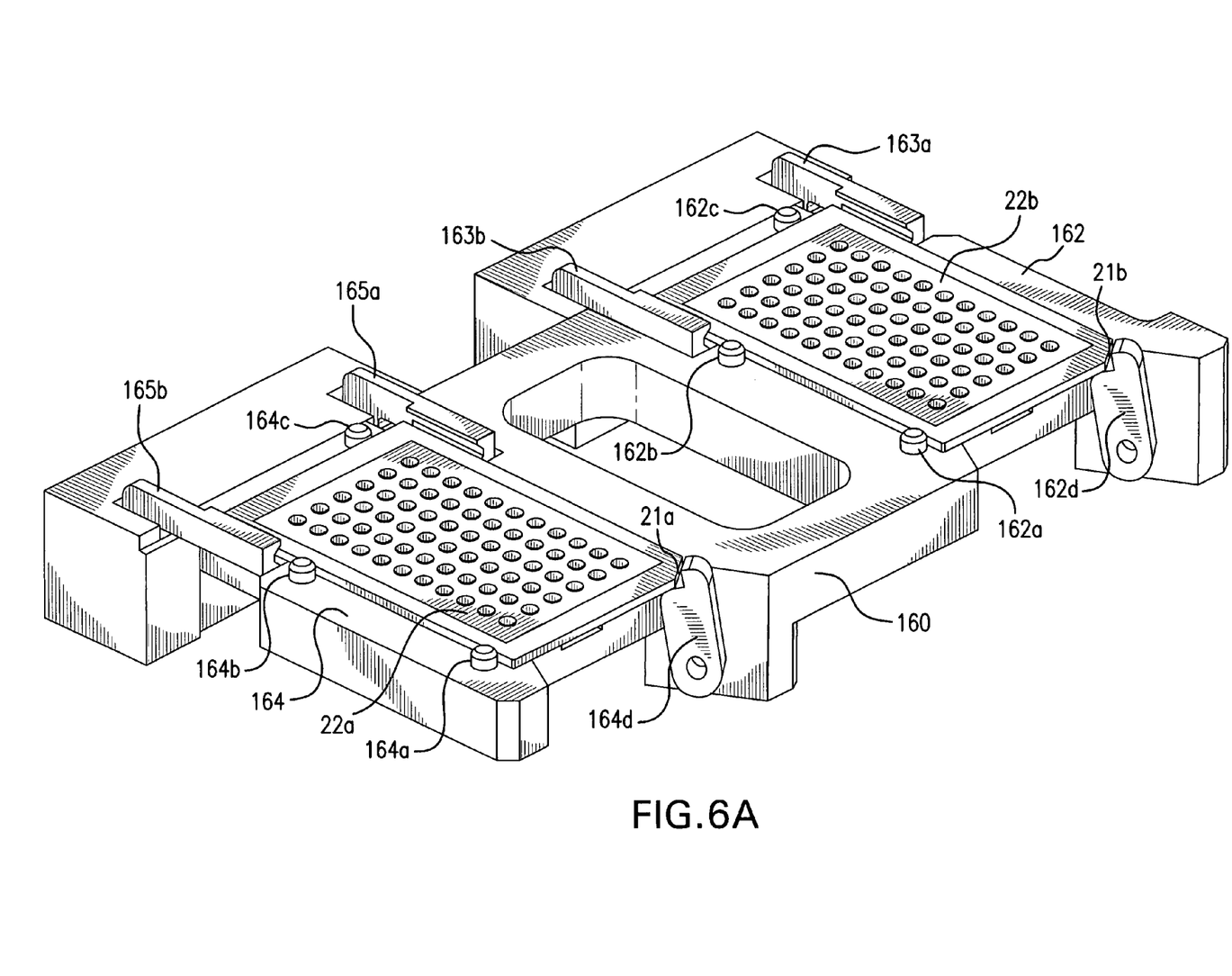
FIG. 6A illustrates a perspective view of a top plate of the slide carriage according to an embodiment and comprising two nests for locating and holding two respective microplates.
Figure 6B:
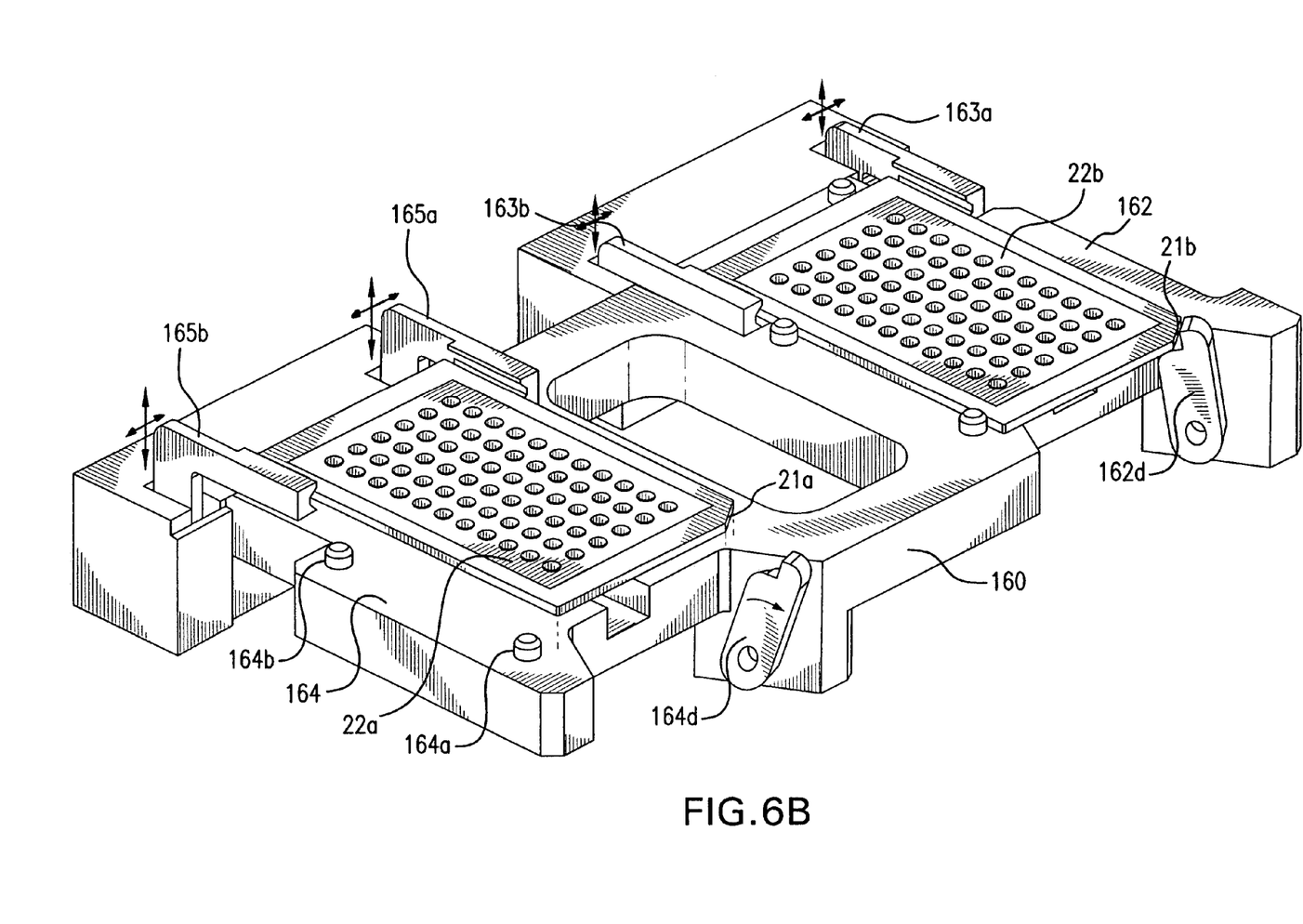
FIG. 6B illustrates a perspective view of the top plate shown in FIG. 6A, wherein a nest-mounted plate gripper associated with one of the nests can be shown holding a microplate in a raised or lifted position.
Figure 7:
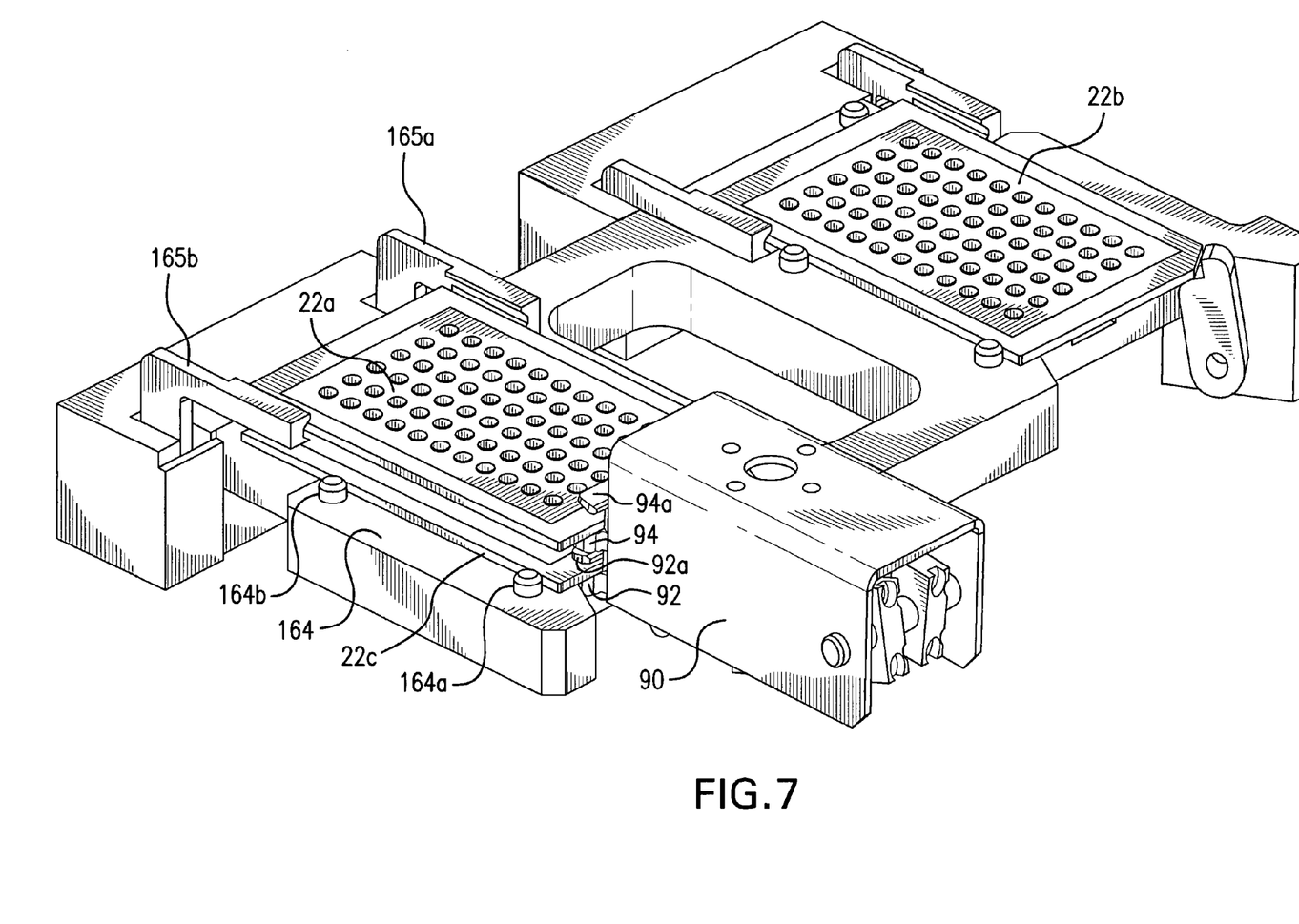
FIG. 7 illustrates a perspective view of the top plate of the slide carriage shown in FIG. 6B, wherein the nest-mounted plate gripper of one nest can be in a raised position and a plate gripper robot can be positioned to place a microplate underneath the microplate raised by the nest-mounted plate gripper.

In order to use this feature at nests 162 and 164 of top plate 160 on slide carriage 60, nest mounted plate grippers 163a and 163b can be provided at nest 162, and nest mounted plate grippers 165a and 165b can be provided at nest 164, to grip and raise microplates 22a and 22b at the respective nests, as shown in FIG. 6A and FIG. 6B. As seen in FIG. 6B nest mounted grippers 165a and 165b can be capable of moving in a horizontal direction adapted to close a distance between the nest mounted grippers 165a and 165b. The microplate 22a can then be gripped. After gripping the microplate 22a, the nest mounted grippers 165a and 165b can be capable of moving in a vertical direction to lift the microplate 22a. The lifting and gripping movements can be provided by means known in the art, for example, a linear motor, an actuator, a cam, a rail, a roller, a slide, or an elevating device. It should be noted that nest mounted grippers 165a and 165b as shown in FIGS. 6B and 7 are not gripping the microplate 22a, for illustration purposes only. The nest mounted grippers 165a and 165b are moved in prior to lifting the microplate 22a.

While the microplate 22a is raised above nest 164, plate gripper robot 90 can approach nest 164 with a new microplate 22c, as shown in FIG. 7. New microplate 22c can be held by lower jaw set 92, 92a comprising lower jaw 92 and lower jaw clamping portion 92a. Plate gripper robot 90 can deposit new microplate 22c, into nest 164. Nest 164 can be located by the microplate 22c through the use of locating pins 164a, 164b, and 164c. Once new microplate 22c has been deposited in nest 164, plate gripper robot 90 can then grip and remove microplate 22a while microplate 22a is held by the raised nest-mounted grippers 165a and 165b, using the upper jaw set 94, 94a including lower jaw 94 and upper jaw clamping portion 94a of plate gripper robot 90.

Figure 8:
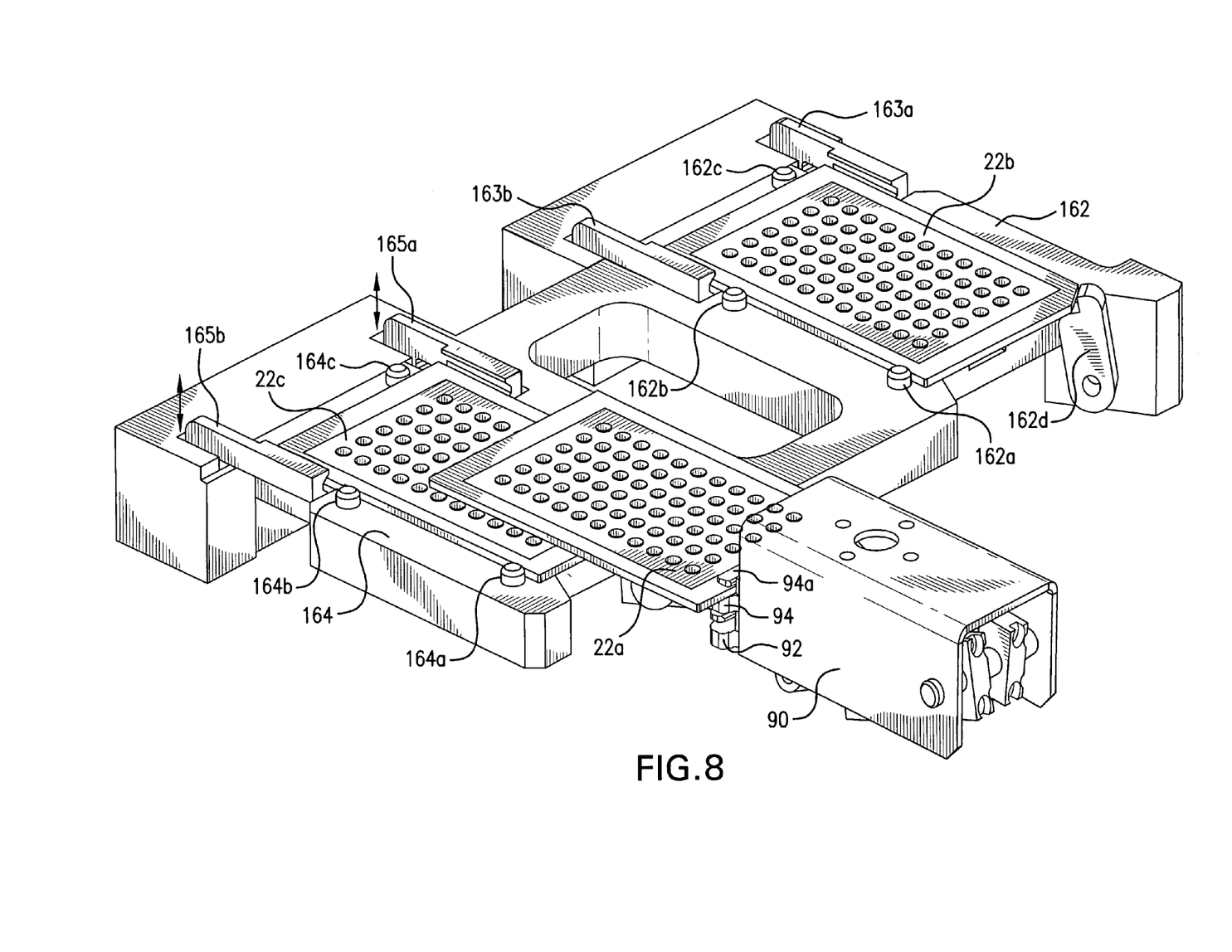
FIG. 8 illustrates a perspective view of the top plate of the slide carriage shown in FIG. 7, after the nest-mounted plate gripper has lowered the microplate and the plate gripper robot has removed the upper microplate.
Figure 9:
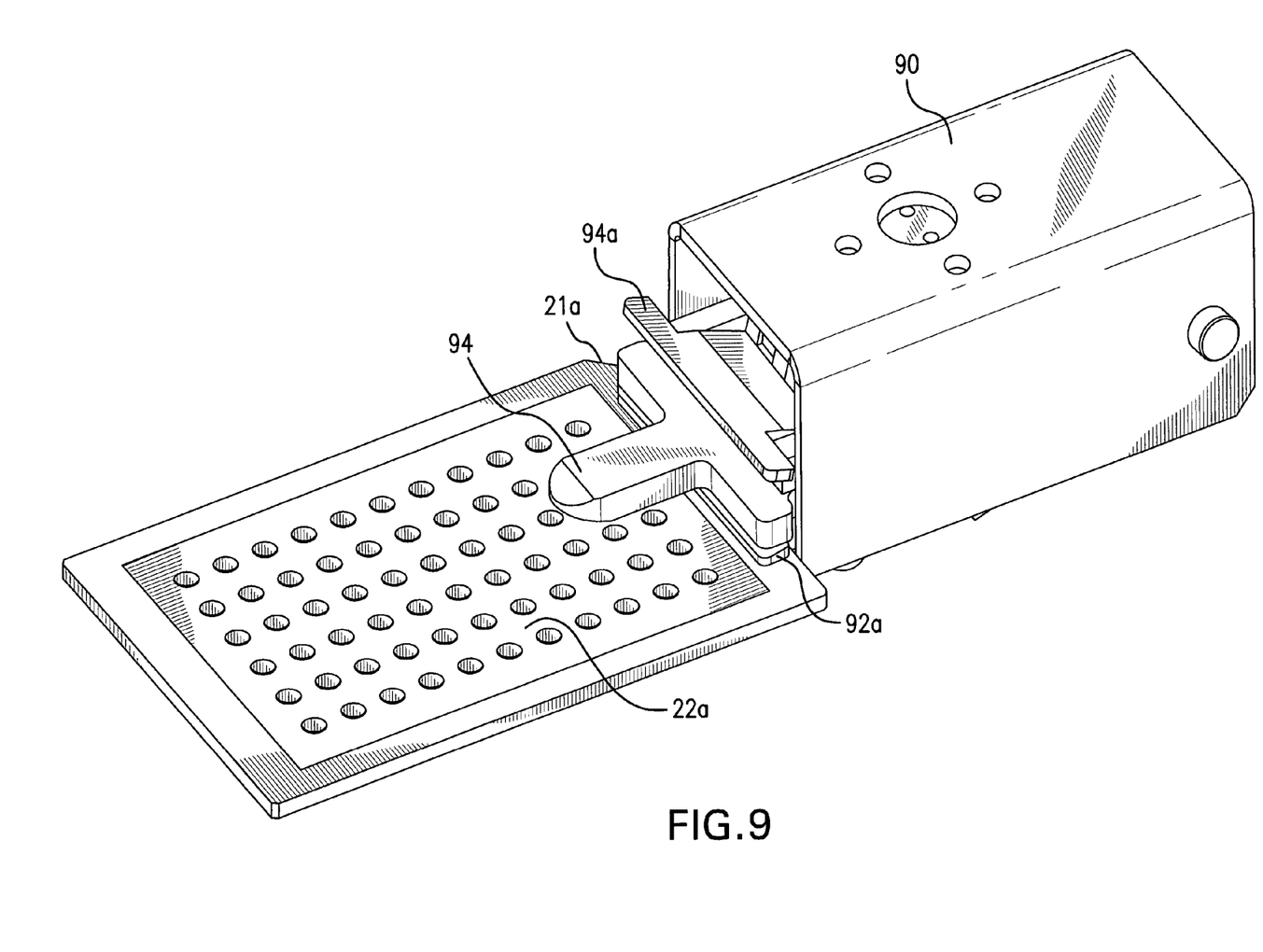
FIG. 9 illustrates a perspective view of the plate gripper robot according to an embodiment and supporting a microplate in a lower jaw of the plate gripper robot.

As shown in FIG. 8, microplate 22a can then be removed by plate gripper robot 90 without interfering with the processing of microplate 22b while microplate 22b is positioned on nest 162 by locating pins 162a, 162b, and 162c, and ratchet 162d.

After exchanging microplates, plate gripper robot 90 can then take microplate 22a that it is holding in its upper jaw set 94, 94a and move the microplate 22a to hotel 122 of carousel 120. Plate gripper robot 90 can place microplate 22a into an open-shelf position, in hotel 120, and at the same time grip another microplate 22 located in a shelf position immediately below the shelf into which microplate 22a can be placed using the lower jaw set 92, 92a. This process can be repeated from the top to the bottom of each hotel 122 on carousel 120. After plate gripper robot 90 has finished with all microplates 22 in hotel 122, plate gripper robot 90 can then shift a microplate 22 from the top position in a respective hotel 122 and place it into the bottom position in the next respective hotel 122. This can allow an empty position to be available at the top of each respective hotel 122 when the process is repeated. The process can be repeated for each hotel 122 of carousel 120. The process can be repeated for each hotel 122 of carousel 120. The process can be repeated as many times as desired or programmed to process each microplate through a spotting process several times.

Hotel 122 can include a plurality of slots, for example, 20, 21, 50, 51, 100, 101, or more slots. The slots can be equidistance from one another. The distance between each slot can be about equal to the distance between lower jaw 92 and lower jaw 94 of plate gripper robot 90. Hotel 122 can be disposed in a rotatable carousel. The hotel can be dispersed on tracks, capable of linear X-Y motion for each hotel. The carousel or the track can be adapted to dispose each hotel into a loading position. The loading position can allow robotic assembly 40 to load and unload microplates 22 from hotel 122.

According to various embodiments, a dispensing head can comprise a plurality of dispensing tips. In various embodiments, a dispensing head can be adapted to aspirate fluid from a source to load one or more of the plurality of dispensing tips. In various embodiments, the table can be configured to support a first microplate in a position to receive fluid dispensed by the dispensing head, and to support a second microplate in a position accessible by the plate-handling device.

According to various embodiments, the fluid distribution system can comprise a microplate storage carousel. The storage carousel can comprise a plurality of racks adapted to hold microplates. The racks can be arranged around the outer periphery of the storage carousel and can be adapted to hold microplates in respective positions that are accessible by the plate-handling device.

In various embodiments, the fluid distribution system can comprise a plate gripper associated with the table and adapted to grip a microplate when the table engages the microplate. The plate gripper can be adapted to lift a microplate to enable the plate-handling device to deposit a second microplate underneath a lifted microplate. The plate-handling device can be adapted to remove a lifted microplate from the one or more plate grippers. The plate-handling device can comprise at least two sets of jaws positioned one over the other, each set of jaws being adapted to grip a respective microplate. The plate-handling device can be adapted to grip a first lifted microplate and remove it from the table substantially simultaneously with depositing a second microplate on the table.

According to various embodiments, the fluid distribution system can comprise a plate gripper associated with the table and adapted to grip a microplate when the microplate is engaged by the table. The plate gripper can be adapted to lift a microplate to enable a first set of jaws of the plate-handling device to deposit a second microplate underneath a lifted microplate, and to enable a second set of jaws of the plate-handling device to remove a lifted microplate from the plate gripper.

In various embodiments, the dispensing head can be fixed in a stationary position. According to various embodiments, the fluid distribution system can comprise a pair of linear motors provided to drive the table in directions parallel to the X-Y plan. In various embodiments, the fluid distribution system can comprise one or more of a pneumatic cylinder or a linear motor adapted to drive the table in the Z direction. The Z direction can be substantially perpendicular to the X-Y plane.

According to various embodiments, a fluid distribution system is provided that can comprise a pair of microplate holders mounted on a three-axis slide carriage, wherein the slide carriage can be mounted for movement on a track. The three-axis slide carriage can be adapted to move the microplate holders in any one or more of three orthogonal directions, for example, in any one or more of an X, a Y, and a Z direction. A fluid dispensing or spotting head can be provided in a fixed position relative to the track and can comprise a plurality of dispensing tips that can each comprise a fluid dispenser, a fluid aspirator, or both a fluid dispenser and a fluid aspirator.

According to various embodiments, the three-axis main slide carriage can comprise at least two non-parallel rails and at least two linear motor driven carriages each engaged with a respective one of the at least two non-parallel rails. Each rail can be arranged at an angle relative to the track. Each of the linear motor driven carriages can be mounted for movement along the track. In various embodiments, at least one of the at least two non parallel rails can be oriented at an angle of from about 40° to about 70° to the track. At least one of the at least two non parallel rails can be oriented at an angle of from about 130° to about 160° relative to the track. In various embodiments, the plate-handling device can be adapted to load plates on and remove plates from the at least two microplate holders.

According to various embodiments, a fluid distribution system is provided, comprising: a track; a three-axis slide carriage mounted for movement along the track, the three-axis slide carriage comprising at least one microplate holder and at least two non-parallel rails arranged in a fixed position with respect to one another; at least two linear motor-driven carriages each mounted for movement along the track and each engaged with a respective one of the at least two non-parallel rails; and a dispensing head positioned relative to the track and comprising a plurality of dispensing tips each adapted to dispense a fluid. Each rail can be arranged at an angle relative to the track. The at least two linear motor-driven carriages can be adapted to simultaneously move in the same direction, simultaneously move toward one another, and simultaneously move away from one another.

In various embodiments, a first one of the at least two non-parallel rails can be arranged at an acute angle with respect to the track and a second of the at least two non-parallel rails can be arranged at an obtuse angle with respect to the track. The at least one microplate holder can comprise two or more microplate holders configured side-by-side. In various embodiments, the fluid distribution system can comprise at least one pneumatic cylinder adapted to drive the three-axis slide carriage in at least one direction.

According to various embodiments, a method of distributing fluids to a plurality of microplates can comprise moving at least two microplates on a table into relationship with a fluid dispensing head comprising a plurality of dispenser tips, such that at least a first of the at least two microplates can be positioned to receive fluid from the dispensing head while at least a second of the at least two microplates can be accessible by a plate-handling device. The method can further comprise dispensing fluid from the dispensing head to a plurality of locations on the first microplate while the second of the microplates can be exchanged with a new plate using the plate-handling device. According to various embodiments, the method can further comprise moving the pair of microplates away from the head, moving a source of fluid into a position adjacent the dispensing head, and aspirating fluid from the source of fluid into the plurality of dispensing tips of the dispensing head.

In various embodiments, the method can comprise moving the at least two microplates away from the dispensing head, moving a source of wash fluid to a location adjacent the dispensing head, and aspirating the washing fluid into the plurality of dispensing tips. In various embodiments, the method can comprise expelling the wash fluid out of the plurality of dispensing tips.

According to various embodiments, one or more of the actuators, solenoids, cams, valves, motors, other means known in the art, or any combinations thereof, can be adapted for use with command and control protocols. The command and control protocols can be implemented by software running on a general-purpose computer. The computer can be equipped with automation control software and a common device.

A control computer (not shown) can integrate the operation of the various assemblies, for example through a program written in an event driven language for example, LABVIEW® or LABWINDOWS® (National Instruments Corp., Austin, Tex.). In particular, the LABVIEW software provides a high level graphical programming environment for controlling instruments. U.S. Pat. Nos. 4,901,221; 4,914,568; 5,291,587; 5,301,301; 5,301,336; and 5,481,741, each expressly incorporated herein by reference, disclose various aspects of the LABVIEW graphical programming and development system. The graphical programming environment disclosed in these patents allows a user to define programs or routines by block diagrams, or "virtual instruments." As this is done, machine language instructions can be automatically constructed which characterize an execution procedure corresponding to the displayed procedure. Interface cards for communicating the computer with the motor controllers are also available commercially, e.g., from National Instruments Corp.

According to various embodiments, the microplates can be multiwell plates, wherein each well can comprise a fluid retainment region, for example, a tube, a vial, a container, a channel in a substrate, a hydrophilic portion on a substrate surrounded by a hydrophobic portion, a capillary narrow enough to hold a fluid by capillary forces, or any combination thereof. According to some embodiments the source of fluid can comprise source plate, for example, a multiwell plate. The microplate and/or the source place can comprise 24, 48, 96, 192, 384, 768, 1536, 3072, 6144, 12288, or more wells.

Other embodiments of the present teachings will be apparent to those skilled in the art from consideration of the present specification and practice of the present teachings.

What is claimed is:

1. A fluid distribution system comprising:
   a table adapted to engage at least two microplates in a side-by-side arrangement, the table being movable in an X-Y plane and in a Z direction toward and away from the X-Y plane;
   a dispensing head adapted to dispense fluids to at least one microplate while the at least one microplate is on the table;
   a plate-handling device adapted to selectively pick up a microplate from the table and deposit a microplate on the table, wherein the plate-handling device comprises at least two sets of jaws positioned one over the other, each set of jaws being adapted to grip a respective microplate; and
   a plate gripper associated with the table and adapted to grip a microplate when the microplate is engaged by the table and adapted to lift a microplate to enable a first set of jaws of the plate-handling device to deposit a second microplate underneath a lifted microplate, and to enable a second set of jaws of the plate-handling device to remove a lifted microplate from the plate gripper.

2. The fluid distribution system of claim 1, wherein the plate-handling device is adapted to grip a first lifted microplate and remove it from the table substantially simultaneously with depositing a second microplate on the table.

3. The fluid distribution system of claim 1, wherein the table further comprises a top plate comprising:
   at least two microplate nests for locating and holding the at least two microplates in a side-by-side arrangement;
   at least two ratchets adapted to engage and locate a respective microplate in a respective microplate nest and also rotate away from the respective microplate; and
   plate grippers adapted to grip a respective microplate and lift the microplate from the respective nest while the respective ratchet is rotated away from the respective microplate.

4. The fluid distribution system of claim 1, wherein the dispensing head is fixed in a stationary position.

5. The fluid distribution system of claim 1, farther comprising:
   a pair of linear motors provided to drive the table in directions parallel to the X-Y plane; and
   one or more of a pneumatic cylinder or a linear motor adapted to drive the table in the Z direction, wherein the Z direction is substantially perpendicular to the X-Y plane.

6. The fluid distribution system of claim 1, further comprising a microplate storage carousel, wherein the storage carousel comprises a plurality of racks adapted to hold microplates wherein the racks are arranged around the outer periphery of the storage carousel and are adapted to hold microplates in respective positions that are accessible by the plate-handling device.

* * * * *